(12) United States Patent
Kim et al.

(10) Patent No.: US 11,975,211 B2
(45) Date of Patent: May 7, 2024

(54) ELECTRIC FIELD CANCER TREATMENT APPARATUS AND METHOD USING ROTATING ALTERNATING CURRENT ELECTRIC FIELD

(71) Applicants: FIELDCURE CO., LTD., Seoul (KR); KOREA UNIVERSITY RESEARCH AND BUSINESS FOUNDATION, Seoul (KR)

(72) Inventors: Jong Hyun Kim, Seoul (KR); Geon Oh, Seoul (KR); Hee Hun Sung, Seoul (KR); Myong Geun Yoon, Gyeonggi-do (KR)

(73) Assignees: FIELDCURE CO., LTD., Seoul (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 18/038,708

(22) PCT Filed: Jan. 5, 2021

(86) PCT No.: PCT/KR2021/000061
§ 371 (c)(1),
(2) Date: May 25, 2023

(87) PCT Pub. No.: WO2022/114383
PCT Pub. Date: Jun. 2, 2022

(65) Prior Publication Data
US 2023/0398366 A1    Dec. 14, 2023

(30) Foreign Application Priority Data
Nov. 25, 2020 (KR) .................. 10-2020-0160333

(51) Int. Cl.
*A61N 1/40* (2006.01)
(52) U.S. Cl.
CPC ..................... *A61N 1/40* (2013.01)
(58) Field of Classification Search
CPC ........................................ A61N 1/40
See application file for complete search history.

(56) References Cited

U.S. PATENT DOCUMENTS

| 8,244,345 B2 | 8/2012 | Palti |
| 9,655,669 B2 | 3/2017 | Palti et al. |

(Continued)

FOREIGN PATENT DOCUMENTS

| JP | 2007-271741 | 10/2007 |
| KR | 10-2017-0115033 | 10/2017 |

(Continued)

OTHER PUBLICATIONS

International Search Report dated Aug. 13, 2021 for PCT/KR2021/000061, 4 pages.
(Continued)

*Primary Examiner* — Mark W. Bockelman

(57) ABSTRACT

An electric field cancer treatment apparatus using a rotating alternating current (AC) electric field according to an embodiment of the present disclosure includes a plurality of electrode pairs configured to transmit AC electric fields to a target area in a body, a plurality of AC electric field generators respectively connected to the plurality of electrode pairs and configured to generate AC electric fields to be applied to the plurality of electrode pairs, and a controller configured to control generation of AC electric fields by the plurality of AC electric field generators.

7 Claims, 2 Drawing Sheets

(56) References Cited

U.S. PATENT DOCUMENTS

| | | | |
|---|---|---|---|
| 11,691,006 B2 * | 7/2023 | Schmidt | A61B 5/0538 |
| | | | 607/62 |
| 2010/0324547 A1 | 12/2010 | Palti | |
| 2011/0137229 A1 | 6/2011 | Palti et al. | |
| 2017/0258518 A1 | 9/2017 | Azure | |
| 2019/0117975 A1 | 4/2019 | Grossman et al. | |

FOREIGN PATENT DOCUMENTS

| | | |
|---|---|---|
| KR | 10-2018-0133431 | 12/2018 |
| KR | 10-2019-0022861 | 3/2019 |
| KR | 10-2022-0055065 | 5/2022 |

OTHER PUBLICATIONS

Kirson, Eilon D., et al. "Disruption of cancer cell replication by alternating electric fields." Cancer research 64.9 (2004): 3288-3295.

Kirson, Eilon D., et al. "Alternating electric fields arrest cell proliferation in animal tumor models and human brain tumors." Proceedings of the National Academy of Sciences 104.24 (2007): 10152-10157.

Hottinger, Andreas F., Patricia Pacheco, and Roger Stupp. "Tumor treating fields: a novel treatment modality and its use in brain tumors." Neuro-oncology 18.10 (2016): 1338-1349.

Wenger, Cornelia, et al. "A review on tumor-treating fields (TTFields): clinical implications inferred from computational modeling." IEEE reviews in biomedical engineering 11 (2018): 195-207.

Berkelmann, Lukas, et al. "Tumour-treating fields (TTFields): Investigations on the mechanism of action by electromagnetic exposure of cells in telophase/cytokinesis." Scientific reports 9.1 (2019): 1-11.

Zhao, Min, John V. Forrester, and Colin D. McCaig. "A small, physiological electric field orients cell division." Proceedings of the National Academy of Sciences 96.9 (1999): 4942-4946.

Korean Office Action dated Jan. 9, 2023, corresponding to Korean Patent Application No. 10-2020-0160333.

Korean Notice of Allowance dated Mar. 29, 2023, corresponding to Korean Patent Application No. 10-2020-0160333.

* cited by examiner

ELECTRIC FIELD CANCER TREATMENT APPARATUS AND METHOD USING ROTATING ALTERNATING CURRENT ELECTRIC FIELD

This application claims the priority of Korean Patent Application No. 10-2020-0160333, filed on Nov. 25, 2020 in the KIPO (Korean Intellectual Property Office), the disclosure of which is incorporated herein entirely by reference. Further, this application is the National Stage application of International Application No. PCT/KR2021/000061, filed on Jan. 5, 2021, which designates the United States and was published in Korean. Each of these applications is hereby incorporated by reference in their entirety into the present application.

TECHNICAL FIELD

The present application relates to an electric field cancer treatment apparatus and method using a rotating alternating current (AC) electric field, and more particularly, to an electric field cancer treatment apparatus and method for maximizing a therapeutic effect by rotating an electric field transmitted to tumor cells in a human body.

BACKGROUND ART

Cancer treatment methods using electromagnetic waves remove tumors by using different principles according to treatment frequency bands. For example, an X-ray frequency band near $10^{10}$ MHz uses the principle of killing cancer cells by cutting a DNA double helix, and an electromagnetic wave of 10 MHz uses the principle of generating heat in a tumor and removing the tumor.

An electric field cancer therapy (tumor treating fields (TTFields)), first reported in 2004, is a treatment technology using the principle of delaying cell division by delivering low-intensity (1 to 3 V/cm), intermediate-frequency band (50 to 500 kHz), alternating electric fields to dividing tumor cells and killing them (see Non-Patent Document 1 [Kirson 2004] and Non-Patent Document 2 [Kirson 2007]). Since an electric field cancer treatment device for patients with recurrent glioblastoma multiform brain tumors was approved by the U.S. FDA in 2011, despite its short history, it has received so much attention that as of 2020, it is being treated in more than 1000 treatment centers around the world.

According to Non-Patent Document 1 [Kirson 2004], Non-Patent Document 2 [Kirson 2007], and Non-Patent Document 3 [Hottinger 2016], the mechanism of action of an electric field cancer therapy is explained by dielectrophoresis of dividing cells. In cells undergoing mitosis, a cleavage furrow is formed in the center of a mother cell during anaphase and telophase when two daughter cells are formed. In this case, when an electric field is applied parallel to a cell division axis, the distribution of electric field lines in the cell becomes non-uniform. That is, a line density increases toward the cleavage furrow. A non-uniform electric field applied to proteins having polarity is forced toward a greater line density. This process known as dielectrophoresis interferes with cell division ability and induces cell death (apoptosis). In order to increase a therapeutic effect from this mechanism of action, the following two points need to be considered.

First, a magnitude of an electric force applied to proteins having polarity in dividing cells is maximized at a specific frequency, and an optimal frequency depends on the size of a cancer cell. Non-Patent Document 4 [Wenger 2018] shows that a maximum value of an electric field in a cleavage furrow occurs at a lower frequency as the size of a cell increases through finite element modeling. Using this relationship between the size of a cell and an optimal frequency, Patent Document 4 [U.S. Pat. No. 9,655,669] discloses a method of approximating an average cell size from the impedance of tumor tissue and changing to an appropriate treatment frequency at regular time intervals. Considering the distribution of tumor cell sizes, it is necessary that treatment frequencies should be distributed within a certain range. In this regard, Patent Document 3 [U.S. Pat. No. 8,244,345] discloses a method of continuously changing a treatment frequency over time within a certain range or alternately delivering a plurality of treatment frequencies.

Second, a therapeutic effect of an electric field cancer therapy is related to an angle between a direction of an electric field and a direction of a division axis. When the two directions coincide, division is maximally hindered, and when the two directions intersect at right angles, division is hardly hindered. Non-Patent Document 4 [Wenger 2018] shows that a maximum value of an electric field in a cleavage furrow dramatically changes according to an angle between a cell division axis and a direction of the electric field. However, because the cell division axis is random, in order to maximize a therapeutic effect, there was used a method of connecting two pairs of electrode arrays crossing at 90 degrees or a plurality of electrode arrays with different directions to a multiplexer and alternating the electrode array pairs at regular intervals to change a direction of an electric field. Non-Patent Document 5 [Berkelmann 2019] shows that in a BT4Ca cell line experiment, the effect is best when an alternating period is 60 seconds rather than when an electric field is applied only in a certain direction. Also, Non-Patent Document 6 [Zhao 1999] found that a division axis is random when there is no electric field, but under an electric field, the division axis is arranged similar to a direction of the electric field. However, this is limited to a direct current (DC) electric field.

In other words, conventional technologies use a method of additionally changing a frequency or amplitude while periodically changing a direction of an electric field by using a multiplexer.

For example, Patent Document 1 [KR 10-2018-0133431] discloses a method of alternately applying a treatment frequency that inhibits mitosis and a frequency that inhibits mobility in order to hinder the spread of cancer cells, and in addition, differentiating amplitudes of two signals and changing a direction of an electrode array over time.

Also, Patent Document 2 [KR 10-2019-0022861] discloses a method of attaching first and second electrode array sets to the front and the back in a longitudinal direction, respectively, in order to treat a tumor in a body part of a subject with a longitudinal axis.

Also, Patent Document 3 [U.S. Pat. No. 8,244,345] discloses a method of alternately changing a direction of an electric field at each treatment frequency while alternately transmitting a plurality of treatment frequencies.

According to the conventional technologies, in order to increase a therapeutic effect, a direction of an electric field may be alternately changed to tumor cells in a body by alternately applying alternating current (AC) to a plurality of electrode array sets at regular intervals by using an electric field generator and a multiplexer, and a frequency and a magnitude of the AC applied to each electrode array set may be determined to be the same or different.

However, as described above, considering that the best therapeutic effect is shown when a cell division axis and a direction of an electric field exactly coincide (in-phase electric fields) and there is no therapeutic effect when they cross at 90 degrees (out-phase electric fields), because effective treatment may be expected only when an angle between the cell division axis and the direction of the electric field is within a certain range from 0°, a conventional method of alternately using a plurality of electrode array sets inevitably has a limitation in that it is difficult to expect effective death of cancer cells outside an effective angle range of each electrode array pair.

(Patent Document 1) Novocure Limited, "Reducing mobility of cancer cells using tumor treating fields (TTFields)", Korean Patent Publication No. 10-2018-0133431, published on Dec. 14, 2018.

(Patent Document 2) Novocure Limited, "Arrays for longitudinal delivery of tumor treatment fields to a body", Korean Patent Publication No 10-2019-0022861, published on Mar. 6, 2019.

(Patent Document 3) Novocure Ltd, St. Helier, "Treating a tumor or the like with electric fields at different frequencies." U.S. Pat. No. 8,244,345, published on Aug. 14, 2012.

(Patent Document 4) Novocure Ltd, "Optimizing treatment using TTFields by changing the frequency during the course of long term tumor treatment", U.S. Pat. No. 9,655,669, published on May 23, 2017.

(Non-Patent Document 1; Kirson 2004) Kirson, Eilon D., et al. "Disruption of cancer cell replication by alternating electric fields." Cancer research 64.9 (2004): 3288-3295.

(Non-Patent Document 2; Kirson 2007) Kirson, Eilon D., et al. "Alternating electric fields arrest cell proliferation in animal tumor models and human brain tumors." Proceedings of the National Academy of Sciences 104.24 (2007): 10152-10157.

(Non-Patent Document 3; Hottinger 2016) Hottinger, Andreas F., Patricia Pacheco, and Roger Stupp. "Tumor treating fields: a novel treatment modality and its use in brain tumors." Neuro-oncology 18.10 (2016): 1338-1349.

(Non-Patent Document 4; Wenger 2018) Wenger, Cornelia, et al. "A review on tumor-treating fields (TTFields): clinical implications inferred from computational modeling." IEEE reviews in biomedical engineering 11 (2018): 195-207.

(Non-Patent Document 5; Berkelmann 2019) Berkelmann, Lukas, et al. "Tumour-treating fields (TTFields): Investigations on the mechanism of action by electromagnetic exposure of cells in telophase/cytokinesis." Scientific reports 9.1 (2019): 1-11.

(Non-Patent Document 6; Zhao 1999) Zhao, Min, John V. Forrester, and Colin D. McCaig. "A small, physiological electric field orients cell division." Proceedings of the National Academy of Sciences 96.9 (1999): 4942-4946.

DISCLOSURE OF THE INVENTION

Technical Problem

Accordingly, in the technical field, there is a demand for a method for enabling effective treatment by fundamentally excluding an ineffective angle, which is inevitable in an electric field cancer therapy according to the conventional technologies.

Objectives of the present disclosure are not limited thereto, and other unmentioned objectives will be clearly understood by one of ordinary skill in the art to which the present disclosure pertains from the following description.

Technical Solution

In order to solve the problems, there is provided an electric field cancer treatment apparatus using a rotating alternating current (AC) electric field.

The electric field cancer treatment apparatus includes a plurality of electrode pairs configured to transmit AC electric fields to a target area in a body, a plurality of AC electric field generators respectively connected to the plurality of electrode pairs and configured to generate AC electric fields to be applied to the plurality of electrode pairs, and a controller configured to control generation of AC electric fields by the plurality of AC electric field generators, wherein the plurality of AC electric field generators simultaneously apply AC to the plurality of electrode pairs connected to the plurality of AC electric field generators so that a plurality of AC electric fields are simultaneously transmitted, and a direction of an electric field formed by the plurality of AC electric fields and transmitted to the target area rotates over time.

Also, according to another embodiment of the present disclosure, there is provided an electric field cancer treatment method using a rotating alternating current (AC) electric field.

The electric field cancer treatment method includes selecting a frequency and an envelope of a first AC electric field to be transmitted to a target area in a body by a first electrode pair, selecting a frequency and an envelope of a second AC electric field to be transmitted to the target area by a second electrode pair, simultaneously applying a first AC electric field and a second AC electric field respectively by the first electrode pair and the second electrode pair, and rotating an electric field transmitted to the target area by the first AC electric field and the second AC electric field.

In addition, the solution to the above problems does not list all the features of the present disclosure. Various features and advantages and effects of the present disclosure will be understood in more detail with reference to the following specific embodiments.

Advantageous Effects

According to an embodiment of the present disclosure, the death of cancer cells may be more effectively induced by fundamentally excluding an ineffective angle by rotating a treatment electric field.

Effects of the present disclosure are not limited thereto, and other unmentioned technical effects will be apparent to one of ordinary skill in the art from the following description.

BEST MODE FOR CARRYING OUT THE INVENTION

Figure 1:
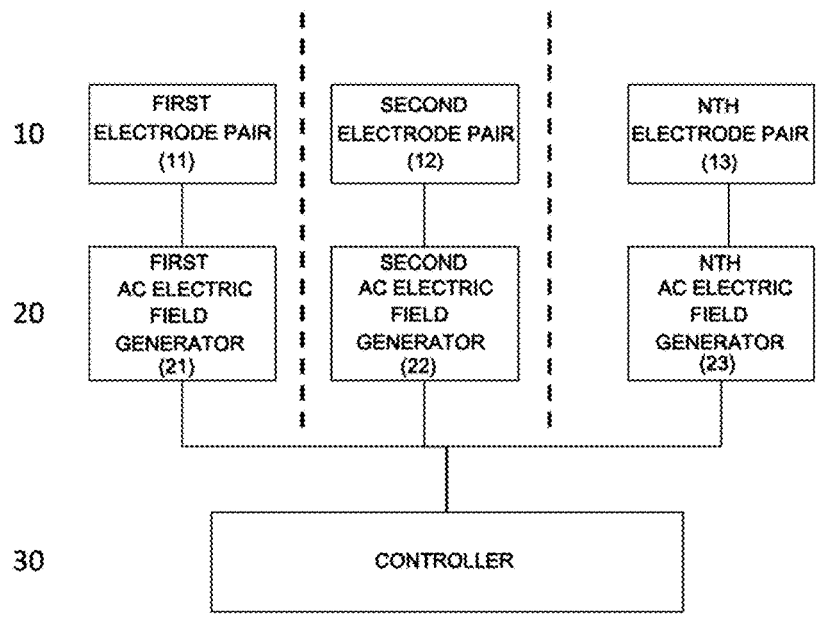
FIG. 1 is a diagram illustrating a configuration of an electric field cancer treatment apparatus using a rotating alternating current (AC) electric field, according to an embodiment of the present disclosure.

Hereinafter, embodiments of the present disclosure will be described in detail with reference to the attached drawings in order to enable one of ordinary skill in the art to embody and practice the present disclosure. While describing the present disclosure, detailed descriptions of related well-known functions or configurations that may blur the points of the present disclosure are omitted. Also, the same reference numerals denote elements having similar functions and actions throughout the drawings.

In addition, throughout the specification, when a portion is referred to as being "connected" to another portion, it may be "directly connected" or may be "indirectly connected" with intervening devices therebetween. When a portion "includes" an element, another element may be further included, rather than excluding the existence of the other element, unless otherwise described.

As described above, the present disclosure provides an electric field cancer treatment apparatus and method for maximizing a therapeutic effect by i) fundamentally excluding an ineffective angle that may occur between a division axis of arbitrary cancer cells and a direction of an electric field and ii) constantly maximizing an intensity of an electric field in each direction.

FIG. 1 is a diagram illustrating a configuration of an electric field cancer treatment apparatus using a rotating alternating current (AC) electric field, according to an embodiment of the present disclosure.

Referring to FIG. 1, an electric field cancer treatment apparatus using a rotating AC electric field according to an embodiment of the present disclosure may include a plurality of electrode pairs 10, a plurality of AC electric field generators 20, and a controller 30. The electrode pairs in the present invention comprises a pair of arrays of electrodes.

The plurality of electrode pairs 10 for transmitting an AC electric field to a target area (e.g., cancer cells or tumor cells) in a body may be located at positions corresponding to the target area of the body so that an angle between directions of electric fields applied by electrode pairs 11, 12, 13 to the target area is included in a preset angle range.

According to an embodiment, when the electric field cancer treatment apparatus includes the first electrode pair 11 and the second electrode pair 12, a first AC electric field may be applied to the target area in a first direction by the first electrode pair 11, and a second AC electric field may be applied to the target area in a second direction by the second electrode pair 12.

In this case, an angle formed between the first direction and the second direction may be included in a range of 60 degrees to 90 degrees, and preferably, the first direction and the second direction may be orthogonal to each other.

Also, the first AC electric field may have a first frequency and a first envelope, and the second AC electric field may have a second frequency and a second envelope.

The first frequency and the second frequency may be selected to interfere with mitosis of cells in the target area. For example, the first frequency and the second frequency may be selected in a range of 50 kHz to 500 kHz.

Also, phases and intensities of the first envelope and the second envelope may be selected so that a direction of an electric field transmitted to the cells of the target area rotates. In this case, a rotation period of the rotating electric field may be selected to be 0.1 seconds or more. Also, a phase difference between the first envelope and the second envelope may be included in a range of 60 degrees to 120 degrees, and preferably may be 90 degrees.

A plurality of AC electric field generators 20 are intended to generate AC electric fields to be applied to the plurality of electrode pairs 10, and AC electric field generators 21, 22, 23 may be respectively connected to the electrode pairs 11, 12, 13.

The AC electric field generators 21, 22, 23 may each have a floating ground so that current flows electrically independently, and should be isolated from each other.

Also, the AC electric field generators 21, 22, 23 may simultaneously apply AC to the electrode pairs 11, 12, 13 connected to the AC electric field generators 21, 22, 23 so that a plurality of AC electric fields are simultaneously transmitted, and a direction of an electric field formed by the plurality of AC electric fields and transmitted to the target area rotates over time.

The controller 30 is intended to control the generation of AC electric fields by the AC electric field generators 21, 22, 23 so that a direction of an electric field transmitted to the target area rotates over time.

According to an embodiment, two electrode pairs that are orthogonal to each other may simultaneously transmit AC electric fields E1 and E2 as shown in Equations 1 and 2 to cancer cells in a target area of a body.

$$E_1 = A_1(t)\sin(\omega t) \qquad \text{[Equation 1]}$$

$$E_2 = A_2(t)\sin(\omega t) \qquad \text{[Equation 2]}$$

Here, $\omega$ is an optimal frequency for inducting cell death by dielectrophoresis, and ranges from 50 kHz to 500 kHz. Also, $A_1(t)$ and $A_2(t)$ respectively denote envelope intensities of the AC electric fields $E_1$ and $E_2$.

In this case, an electric field transmitted to the cancer cells by the two electrode pairs is a vector sum of the AC electric fields $E_1$ and $E_2$.

Also, when the two electric fields are transmitted orthogonal to each other, in order to maintain constant an intensity of an electric field, $A_1(t)$ and $A_2(t)$ should satisfy a relationship of Equation 3. Accordingly, $A_1(t)$ and $A_2(t)$ respectively satisfy Equations 4 and 5. Here, $T_{env}$ denotes a period of an envelope, and $\emptyset$ denotes a phase difference (phase shift) between $A_1(t)$ and $A_2(t)$. Also, $A_0$ denotes an intensity of an electric field transmitted to the cancer cells.

$$A_1^2 + A_2^2 = A_0^2 \qquad \text{[Equation 3]}$$

$$A_1 = A_0 \sin\left(\frac{2\pi}{T_{env}} t\right) \qquad \text{[Equation 4]}$$

$$A_2 = A_0 \sin\left(\frac{2\pi}{T_{env}} t + \emptyset\right) \qquad \text{[Equation 5]}$$

According to another embodiment, three electrode pairs that are orthogonal to each other in a three-dimensional (3D) space may simultaneously transmit AC electric fields to a target area so that an electric field rotates in the 3D space.

In this case, an envelope of an AC electric field applied to each electrode pair should satisfy Equations 6 to 9.

$$A_x^2 + A_y^2 + A_z^2 = A_0^2 \quad \text{[Equation 6]}$$

$$A_x = A_0 \sin(\theta)\cos(\varphi) \quad \text{[Equation 7]}$$

$$A_y = A_0 \sin(\theta)\sin(\varphi) \quad \text{[Equation 8]}$$

$$A_z = A_0 \cos(\theta) \quad \text{[Equation 9]}$$

Here, $\theta$ and $\varphi$ denote time functions included in ranges of $\theta \in [0, \pi]$ and $\varphi \in [0, 2\pi]$.

Figure 2:
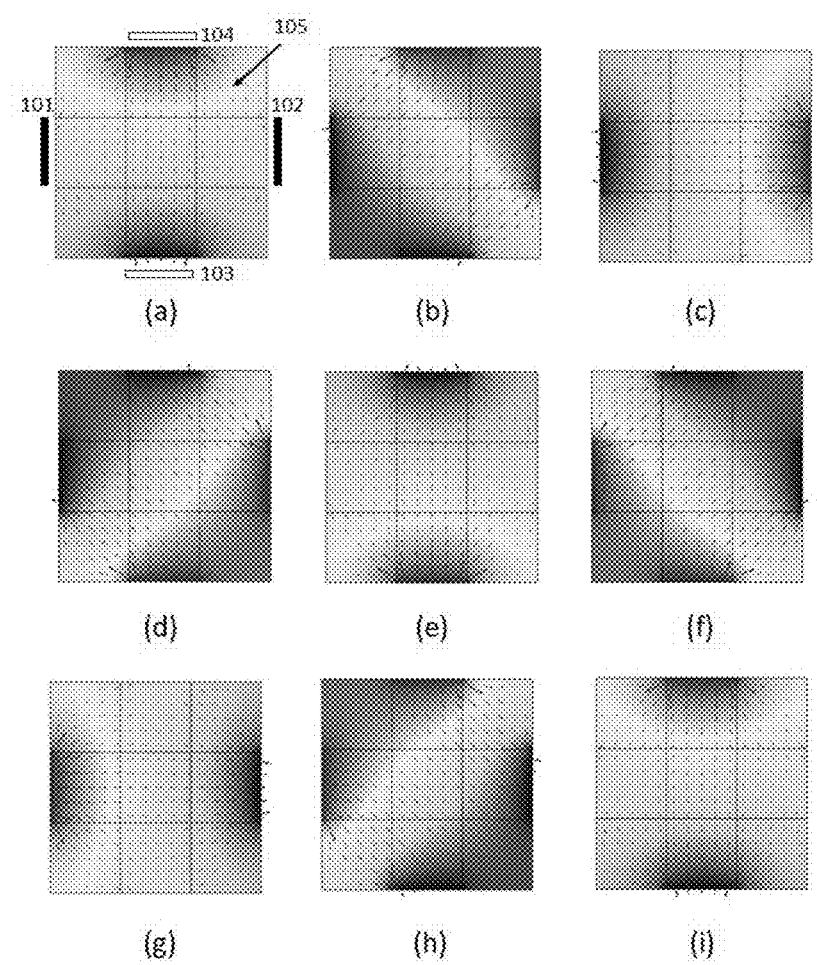
FIG. 2 is a diagram illustrating a direction and a magnitude of an AC electric field applied into a body over time when pieces of current having a phase difference of 90 degree are applied to two electrode pairs in a certain period.

FIG. 2 is a diagram illustrating a direction and a magnitude of an AC electric field transmitted into a body over time when current of a certain period is applied to two electrode pairs to have a phase difference of 90 degrees.

According to an embodiment, envelope current having an envelope period $T_{env}$ of 240 seconds may be applied to two electrode pairs 101 and 102, 103 and 104 attached to a body 105 to have a phase difference of 90 degrees. In this case, a result of simulating a direction and a magnitude of an AC electric field transmitted into the body 105 over time is shown in FIG. 2.

In detail, (a) to (i) of FIG. 2 illustrates electric fields in the body 105 at 30 second intervals during the envelope period, that is, respectively 0, 30, 60, 90, 120, 150, 180, 210, and 240 seconds.

Referring to FIG. 2, it is found that, when current of a certain period is applied to two electrode pairs to have a phase difference of 90 degrees as described above, an electric field of a constant magnitude rotates over time.

Figure 3:
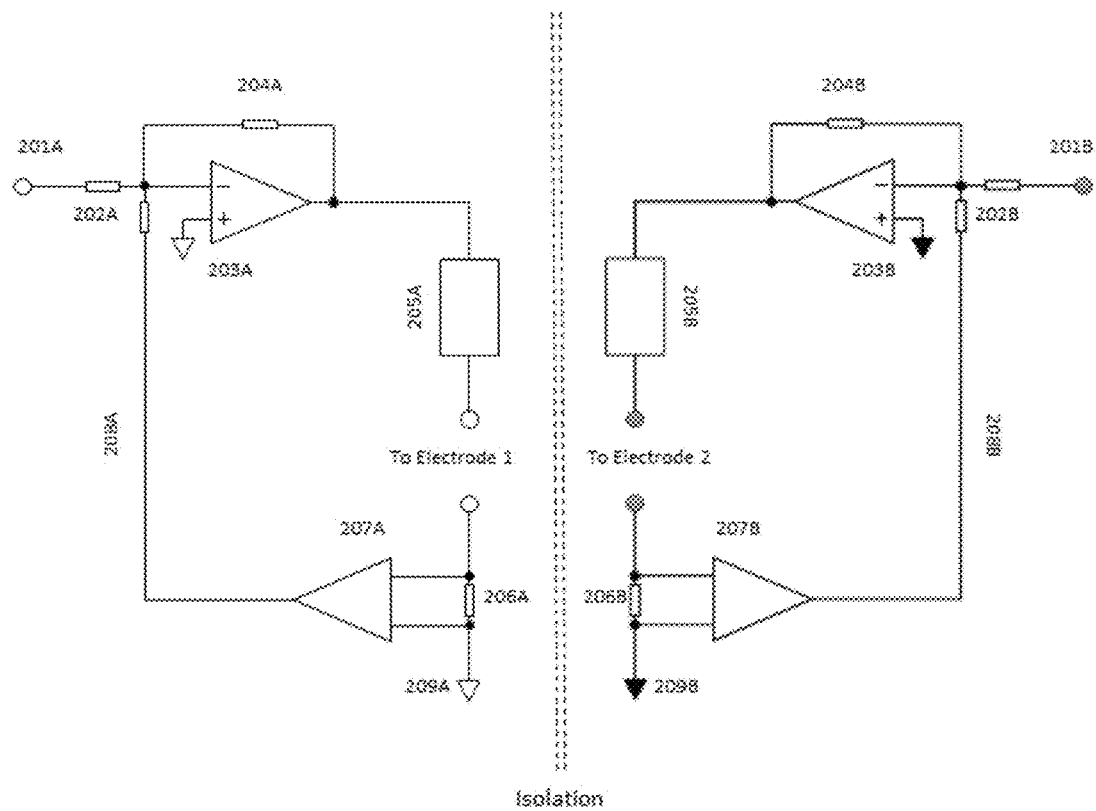
FIG. 3 is a diagram illustrating an AC electric field generator included in an electric field cancer treatment apparatus using a rotating AC electric field, according to an embodiment of the present disclosure.

FIG. 3 is a diagram illustrating an AC electric field generator included in an electric field cancer treatment apparatus using a rotating AC electric field, according to an embodiment of the present disclosure. The AC electric field generator may be implemented to form a closed-loop feedback system.

In detail, current as shown in Equations 10 and 11 may be input as input signals 201A, 201B of AC electric field generators. That is, input signals of the AC electric field generators may be current having envelopes as shown in Equations 4 and 5.

$$I_1 = I_0 \sin\left(\frac{2\pi}{T_{env}} t\right) \sin(\omega t) \quad \text{[Equation 10]}$$

$$I_2 = I_0 \sin\left(\frac{2\pi}{T_{env}} t + \phi\right) \sin(\omega t) \quad \text{[Equation 11]}$$

Differences between the input signals 201A, 201B and feedback signals 208A, 208B may be output through control amplifiers 203A, 203B.

In this case, a bandwidth of the entire closed-loop feedback system may be controlled by feedback capacitors 204A, 204B.

Output terminals of the control amplifiers 203A, 203B may be connected to gate signals of internal FETs of power amplifiers 205A, 205B to control magnitudes of power sources input to the power amplifiers 205A, 205B.

Output terminals of the power amplifiers 205A, 205B are connected to electrode pairs Electrode 1 and Electrode 2 to transmit an electric field into a body.

Current flowing through each electrode is proportional to voltages applied to both terminals of sensing resistors 206A, 206B, and the voltages are converted into the feedback signals 208A, 208B by current/voltage (I/E) converters 207A, 207B and are input back to the control amplifiers 203A, 203B through adder circuits 202A, 202B.

Also, the power sources input to the power amplifiers 205A, 205B should be isolated from each other, and signal grounds 209A, 209B are floating grounds.

Figure 4:
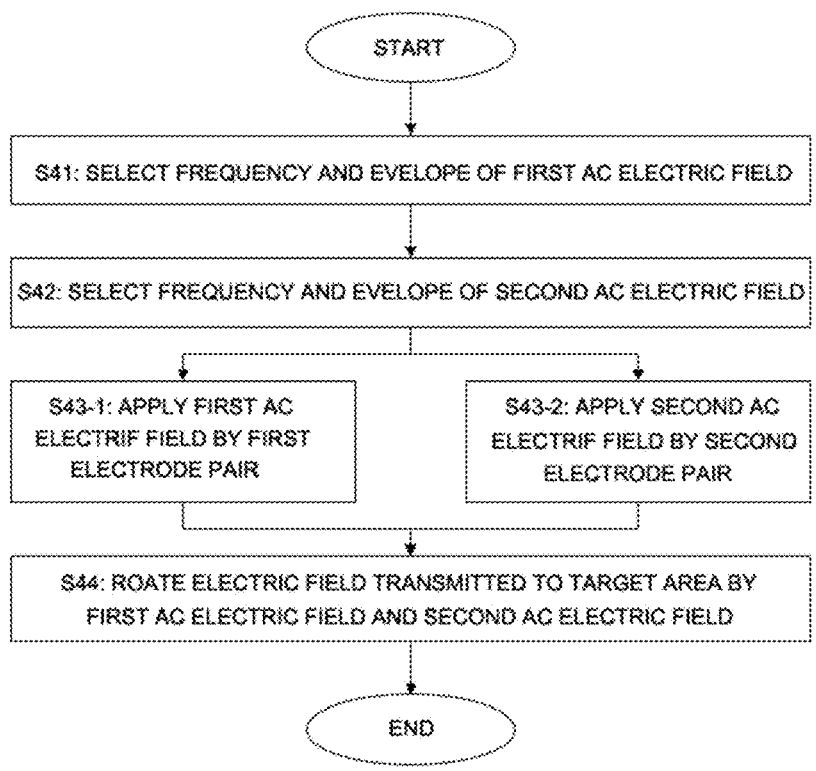
FIG. 4 is a flowchart illustrating an electric field cancer treatment method using a rotating AC electric field, according to another embodiment of the present disclosure.

FIG. 4 is a flowchart illustrating an electric field cancer treatment method using a rotating AC electric field, according to another embodiment of the present disclosure. A method of performing electric field cancer treatment by rotating an AC electric field by using two electrode pairs will be described.

Referring to FIG. 4, first, a frequency and an envelope of a first AC electric field may be selected (S41), and a frequency and an envelope of a second AC electric field may be selected (S42). The frequencies of the first AC electric field and the second AC electric field may be formed to interfere with mitosis of cells of a target area, and phases and amplitudes of the envelopes of the first AC electric field and the second AC electric field may be selected so that a direction of an electric field transmitted to the cells of the target area rotates.

Next, the first AC electric field and the second AC electric field may be simultaneously applied by a first electrode pair and a second electrode pair (S43-1 and S43-2), and an electric field transmitted to the target area by the first AC electric field and the second AC electric field rotates to perform electric field treatment (S44).

The electric field canter treatment method described with reference to FIG. 4 may be performed by the electric field cancer treatment apparatus described with reference to FIG. 1, and a specific method of each step is the same as that described with reference to FIGS. 1 to 3, and thus, a repeated description thereof will be omitted.

The present disclosure is not limited by the above embodiments and the attached drawings. It will be apparent to one of ordinary skill in the art to which the present disclosure pertains that components according to the present disclosure may be substituted, modified, and changed without departing from the technical scope of the present disclosure.

The invention claimed is:

1. An electric field applying apparatus using a rotating alternating current (AC) electric field, comprising:
   a plurality of electrode pairs configured to transmit AC electric fields to a target area in a body;
   a plurality of AC electric field generators respectively connected to the plurality of electrode pairs and configured to generate AC electric fields to be applied to the plurality of electrode pairs; and
   a controller configured to control generation of AC electric fields by the plurality of AC electric field generators,
   wherein the plurality of electrode pairs comprise a first electrode pair and a second electrode pair,
   wherein a first AC electric field is applied to the target area in a first direction by the first electrode pair, and a second AC electric field is applied to the target area in a second direction by the second electrode pair,
   wherein the first AC electric field has a first frequency and a first envelope, and the second AC electric field has a second frequency and a second envelope,
   wherein the first frequency and the second frequency are selected in a range of 50 kHz to 500 kHz to interfere with mitosis of cells in the target area,
   wherein phases and intensities of the first envelope and the second envelope are selected so that a direction of an electric field transmitted to the cells of the target area rotates through angles between the first electrode pair and the second electrode pair.

2. The electric field applying apparatus using a rotating AC electric field of claim 1, wherein the plurality of electrode pairs are adapted to be located at positions corresponding to the target area so that an angle between directions of electric fields applied by the plurality of electrode pairs to the target area is included in a preset angle range.

3. The electric field applying apparatus using a rotating AC electric field of claim 1, wherein a phase difference between the first envelope and the second envelope is included in a range of 60 degrees to 120 degrees.

4. The electric field applying apparatus using a rotating AC electric field of claim 1,
wherein an angle formed between the first direction and the second direction is 90 degrees,
wherein intensities of the first envelope and the second envelope are respectively expressed by equations $$A_1 = A_0 \sin\left(\frac{2\pi}{T_{env}} t\right) \text{ and}$$

$$A_2 = A_0 \sin\left(\frac{2\pi}{T_{env}} t + \phi\right),$$

where $A_1$ and $A_2$ respectively denote intensities of the first envelope and the second envelope,
$T_{env}$ denotes a period of an envelope, and
$\phi$ denotes a phase difference between $A_1$ and $A_2$.

5. The electric field applying apparatus using a rotating AC electric field of claim 1, wherein a rotation period of the rotating electric field is 0.1 seconds or more.

6. The electric field applying apparatus using a rotating AC electric field of claim 1, wherein the plurality of AC electric field generators each have a floating ground so that current flows electrically independently, and is isolated from each other.

7. An electric field applying method using a rotating alternating current (AC) electric field, comprising:
selecting a frequency and an envelope of a first AC electric field to be transmitted to a target area in a body by a first electrode pair;
selecting a frequency and an envelope of a second AC electric field to be transmitted to the target area by a second electrode pair;
simultaneously applying a first AC electric field and a second AC electric field respectively by the first electrode pair and the second electrode pair; and
rotating an electric field transmitted to the target area by the first AC electric field and the second AC electric field,
wherein the first AC electric field has a first frequency and a first envelope, and the second AC electric field has a second frequency and a second envelope,
wherein the first frequency and the second frequency are selected in a range of 50 kHz to 500 kHz to interfere with mitosis of cells in the target area,
wherein phases and intensities of the first envelope and the second envelope are selected so that a direction of an electric field transmitted to the cells of the target area rotates through angles between the first electrode pair and the second electrode pair.

* * * * *